United States Patent
Garnica Rodriguez et al.

(10) Patent No.: US 9,908,118 B2
(45) Date of Patent: Mar. 6, 2018

(54) METHOD FOR FUSING OR CONTACTING REACTOR AND REAGENT DROPLETS IN A MICROFLUIDIC OR MILLIFLUIDIC DEVICE

(71) Applicants: ETABLISSEMENTS J. SOUFFLET, Nogent-sur-Seine (FR); ECOLE SUPERIEURE DE PHYSIQUE ET DE CHIMIE INDUSTRIELLES DE LA VILLE DE PARIS, Paris (FR)

(72) Inventors: Jairo Ivan Garnica Rodriguez, Massy (FR); Laurent Boitard, Paris (FR); Antoine Serge Dominique Drevelle, Romilly (FR); Nicolas Pierre Bremond, Paris (FR); Jérôme Bibette, Paris (FR)

(73) Assignees: ETABLISSEMENTS J. SOUFFLET, Nogent-sur-Seine (FR); ECOLE SUPERIEURE DE PHYSIQUE ET DE CHIMIE INDUSTRIELLES DE LA VILLE DE PARIS, Paris (FR)

( * ) Notice: Subject to any disclaimer, the term of this patent is extended or adjusted under 35 U.S.C. 154(b) by 0 days.

(21) Appl. No.: 15/501,597

(22) PCT Filed: Aug. 5, 2015

(86) PCT No.: PCT/EP2015/068014
§ 371 (c)(1),
(2) Date: Feb. 3, 2017

(87) PCT Pub. No.: WO2016/020414
PCT Pub. Date: Feb. 11, 2016

(65) Prior Publication Data
US 2017/0216844 A1    Aug. 3, 2017

(30) Foreign Application Priority Data
Aug. 6, 2014 (EP) .................... 14306248

(51) Int. Cl.
*B01L 3/00* (2006.01)
*G01N 35/08* (2006.01)

(52) U.S. Cl.
CPC ..... *B01L 3/502784* (2013.01); *B01L 3/50273* (2013.01); *B01L 3/502715* (2013.01);
(Continued)

(58) Field of Classification Search
None
See application file for complete search history.

(56) References Cited

U.S. PATENT DOCUMENTS

2006/0003439 A1*  1/2006  Ismagilov ............. B01F 5/0471
                                                                435/287.2

FOREIGN PATENT DOCUMENTS

WO    WO 2008/079274 A1    7/2008

OTHER PUBLICATIONS

Baroud et al., "Dynamics of microfluidic droplets," Lab on a Chip, vol. 10, No. 16, 2010, pp. 2032-2045.
(Continued)

*Primary Examiner* — Jennifer Wecker
(74) *Attorney, Agent, or Firm* — Birch, Stewart, Kolasch & Birch, LLP (57) ABSTRACT

The present invention discloses a method for fusing or contacting reactor and reagent droplets in a three-phase microfluidic or millifluidic system with one of the phases being continuous, in which the reagent droplet is injected in the droplet train before it coalesces or contacts with the reactor droplet. More specifically, the reagent droplet detaches from the reagent inlet before being in contact with the reactor droplet. The method of the invention involves two successive but not concomitant steps: first producing in the droplet train a droplet of a reagent which breaks-up from the reagent reservoir before the second step of merging. The
(Continued)

invention also discloses a milli/microfluidic device whose equivalent circuit is represented on FIG. 11.

15 Claims, 10 Drawing Sheets

(52) U.S. Cl.
CPC .......... *B01L 2200/0673* (2013.01); *B01L 2300/0645* (2013.01); *B01L 2300/0654* (2013.01); *B01L 2400/0666* (2013.01); *G01N 35/08* (2013.01)

(56) References Cited

OTHER PUBLICATIONS

International Search Report (Form PCT/ISA/210), dated Nov. 2, 2015, for International Application No. PCT/EP2015/068014.
Torza et al., "Three-phase interactions in shear and electrical fields," Journal of Colloid and Interface Science, vol. 33, No. 1, May 1970, pp. 67-83.

* cited by examiner

METHOD FOR FUSING OR CONTACTING REACTOR AND REAGENT DROPLETS IN A MICROFLUIDIC OR MILLIFLUIDIC DEVICE

Droplet-based flow reactors have proven to be of particular value for the controlled synthesis of functional materials whose properties are strongly influenced by the reaction conditions. For instance, significant improvements in product control (with respect to both batch and continuous flow synthesis) have been demonstrated for a broad range of optoelectronic materials including metal nanocrystals, quantum dots and conjugated polymers. To date, however, droplet synthesis has been largely limited to simple one-step procedures, in which all reagents are loaded into the droplets at the outset, greatly restricting the range of chemistries that can be employed. To properly exploit the benefits of droplet flow, and widen the palette of accessible chemistries/materials, there is an obvious need to develop multistep droplet reactors in which reagents can be sequentially added into the flowing droplets as the reaction proceeds.

In a droplet flow process, the continuous phase is a liquid that preferentially wets the channel walls, and the reagent phase is divided into a train of discrete, near-identical low-volume droplets that travel through the channel at a common speed. The composition of the droplets may vary from one droplet to another, when droplets with different active ingredients are desired or when droplets contain a progressive (such as growing) ingredient such as microorganisms, typically spore of fungi. Owing to their small (typically submicroliter) volumes the droplets are extremely uniform with regards to chemical composition and temperature, and so provide a highly controlled environment for carrying out chemical reactions. Moreover, since the droplets are kept away from the channel walls by the continuous phase, the chance of reactor fouling due to precipitation of reagents or products on the channel wall is virtually eliminated, ensuring a stable, unchanging reaction environment.

Droplet fusion is a very important operation for digital micro/millifluidics, as it allows the combination of reagents for the initiation of biological and/or chemical reactions. In a fluidic channel, droplet coalescence requires the removal of the continuous phase separating them. When two droplets come into close contact, a thin liquid bridge forms between the droplets. The high curvature meniscus formed around the bridge creates an imbalance of the surface tension that coalesces the two droplets. Close contact between droplets for a critical minimum amount of time is necessary for coalescence. To achieve droplet fusion, spatial and temporal synchronization are required. Existing droplet fusion technologies exhibit disadvantageous complex channel designs and/or inter-droplet contamination. This invention allows the self-synchronized injection of reagent droplets and their fusion, advantageously their passive fusion, with reactor droplets in three-phase fluidic systems without interdroplet contamination, as well as without contamination of the reagent reservoir, in simple channel designs.

Existing Technologies

Passive Droplet Fusion

Figure 1:
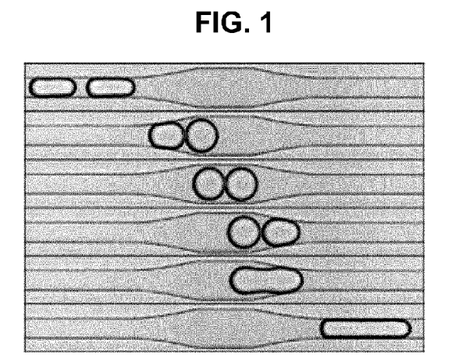
FIG. 1: Geometry-mediated passive droplet fusion (prior art)

The geometry-mediated passive droplet fusion is based on the drainage of the continuous phase in expansion volumes (FIG. 1). This method is characterized by an advantageous low inter-droplet contamination, but requires channels of added design complexity and exhibits lower throughputs than active fusion methods.

Figure 2:
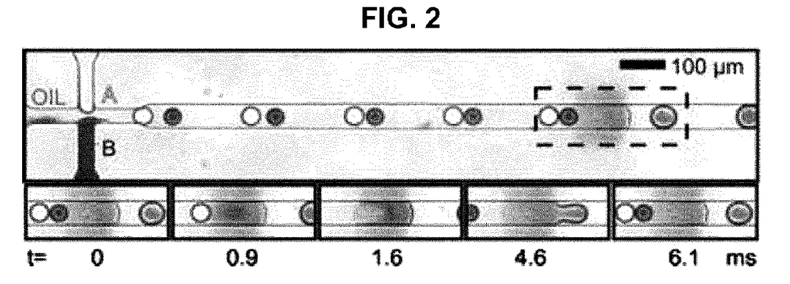
FIG. 2: Surface wettability-induced passive droplet fusion (prior art)

Surface wettability-induced passive droplet fusion (FIG. 2) is based on the use of hydrophilic patches to induce fusion between pairs of aqueous droplets. Despite of not requiring droplet synchronisation, the main disadvantage of this method is the high inter-droplet contamination during the passage through the wetting patch.

Figure 3:
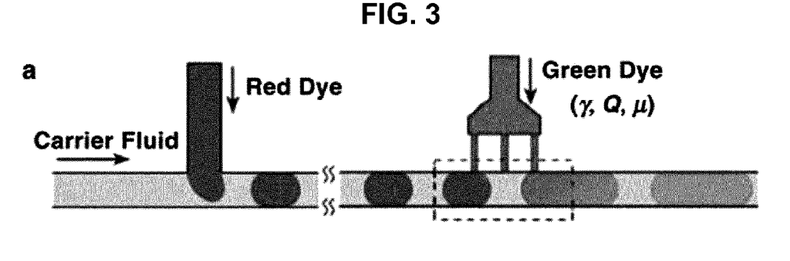
FIG. 3: Reagents added to passing droplets (prior art)

In another passive method, reagents are added to passing droplets (FIG. 3). Although inter-droplet contamination has been reduced (but not stopped) by using hydrophilic narrow channels, this approach has low control of the specific amount of reagent added to a passing droplet as successful reagent injection of substrate requires a careful balance of the volumetric flow rates of the continuous and dispersed phases.

Active Droplet Fusion

Figure 4:
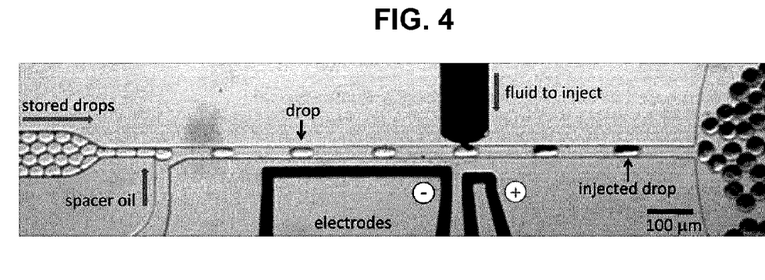
FIG. 4: Picoinjector in an active droplet fusion system by the use of electrodes (prior art)

Active droplet fusion methods are more complex than many passive droplet fusion schemes, since many require fabrication of electrodes and precise timing of electrical signals in order to fuse droplets. These methods use electricity to generate the surface tension instabilities required for droplet coalescence. One of the most advanced designs is the picoinjector shown in FIG. 4. When a droplet passes by the picoinjector, the electrodes are activated, producing a water/oil interface thin-film instability that allows the reagent to enter the drop. High throughput (several kilohertz) and subpicoliter injection precision were claimed. The main inconvenient of this method is the possible contamination of the injection solution reservoir during in situ fusion with a passing droplet. From the use of electricity come concerns of biocompatibility of electrical signals on biological molecules, such as DNA or proteins.

Three-Phase Microfluidic System

WO2008/79274 discloses a three-phase microfluidic system comprising a continuous phase, reactor droplets and a spacer. The spacer is formed by immiscible liquids or hydrophobic particles to prevent coalescence of reactor droplets. This application also discloses the addition of reagent droplet by injection using a T-junction microfluidic device but does not specifically describes how the injection occurs. In particular it does not teach or suggest to break-up the reagent droplet before coalescence. The method used in this document will not prevent contamination, in particular contamination of the reservoir but also contamination between the flowing droplets in particular when the train is not regular. The method used in this document is not self-synchronized and will not allow to control, nor to adjust, the volume of the reagent droplet on case by case basis. In addition, the method used in this document will not allow to select the "target" reactor droplet.

DESCRIPTION OF THE FIGURES

FIG. 15: Variable volume injection—calculated $V_T/V_R$ ratio FIG. 16. Enhancement of meniscus retraction by capacitor introduction. Without air bubble (left). With air bubble (right). 16a: water, 16b: Fluorinated oil, 16c: meniscus, 16d: air bubble The present invention discloses for the first time a method for fusing or contacting reactor and reagent droplets in a three-phase microfluidic or millifluidic system, in which the reagent droplet, injected in the train with the help of a lateral inlet named injector, is detached from the reagent reservoir before coalescence with the reactor droplet. More specifically, the reagent droplet detaches before being in contact with the reactor droplet. The method of the invention involves two successive but not concomitant steps: first producing in the train a droplet of a reagent which detaches before the second step of merging. By the method of the invention, one forms in situ reagent droplet, which formation can be synchronized and, if required, selective. The reagent droplet is formed in-situ, the resulting droplet is hanging at the injection point (lateral inlet) and breaks-up from the reagent reservoir before the reactor droplet reaches the injection point.

By the method of the invention droplets are fused without contamination, namely without contamination of the reservoir and without cross-contamination between the droplets, even in presence of microorganisms in droplets, and even more in presence of fungi.

The method of the invention can be used for active or passive fusion, meaning that the use of electrodes for fusing droplets is optional, and more advantageously no electrode is used (passive fusion). In addition, the channel of the microfluidic or millifluidic device can be regular. In particular, it does not comprise bifurcation geometry at the place where the reagent droplet is added, and for example the channel can be a rounded channel without bifurcation geometry.

The method of the invention can be used for regular or irregular train. In particular, by the method of the invention, one is able to operate a train comprising reactors that are not equidistant.

Micro/millifluidic means microfluidic or millifluidic. Microfluidics refers systems in which small volumes of fluids are handled in micro metric scale channels/tubes. Millifluidics refer to systems in which small volumes of fluids are handled in milli metric scale channels/tubes.

The invention is directed to a method for fusing or contacting reactor and reagent droplets in a microfluidic or millifluidic device, comprising the steps of (a) In the channel of said microfluidic or millifluidic system, generating a three-phase micro/millifluidic train comprising a continuous phase, at least two reactor droplets, and at least one spacer plug between two reactor droplets $A_n$ and $A_{n+1}$, wherein n is an integer≥0

(b) injecting with the help of a lateral inlet named injector, into the train, reagent in a non-wetting single droplet B, wherein said droplet B is generated in situ during the passage at the injection point of the spacer plug directly preceding reactor droplet $A_{n+1}$, wherein the droplet B is detached from the injection point before the reactor droplet $A_{n+1}$ reaches the injection point with the formation of a reagent fluid meniscus at the injector end, and wherein the reagent fluid meniscus is retracted within the lateral inlet when the reactor droplet $A_{n+1}$ is at the injection point;

(c) then, fusion or contact of the droplet B with reactor droplet $A_{n+1}$ away from the injection point (d) when n>1, reiteration of steps (b) and (c).

The channel of said microfluidic or millifluidic system has a cylindrical geometry or a planar one. In the following description, we will refer to a cylindrical geometry and thus we will define the size of the channel by reference to its diameter. These references should be replaced by height and the width of the channel where the train of drops circulates for a planar geometry.

In the present description, it is meant by "injection point" the droplet B generation point that corresponds to the injector location. Hereafter, droplet B is also called reagent droplet.

In the description, the terms "reagent droplet", "reagent fluid" are used to define the droplet, respectively the fluid, which comprises the reagent. Similarly, the terms "reactor droplet", "reactor fluid" are used to define the droplet, respectively the fluid, which comprises the reactor.

The term "plug" is used to define a droplet whose volume V is larger than $\pi D^3/6$, where D is the diameter of the tube where the train of drops circulates for a cylindrical geometry, or larger than $\pi H W^2/4$ where H and W stand respectively for the height and the width of the channel where the train of drops circulates for a planar geometry.

Figure 5:
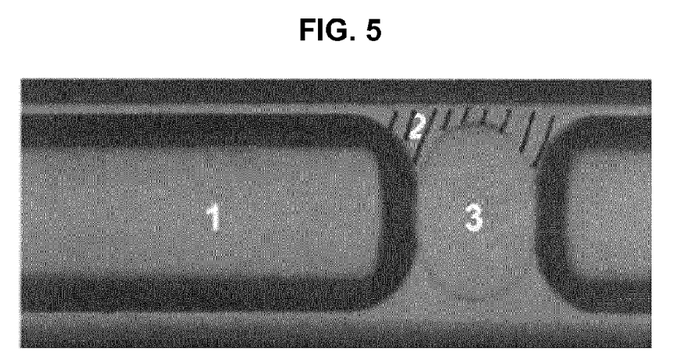
FIG. 5: three-phase micro/millifluidic system of the invention

In the method of the invention, the micro/millifluidic system comprises at least three phases: the continuous phase (2), the spacer phase (1) and the reactor droplet phase (3) (FIG. 5). The zone in the continuous phase between the spacer plug and the reagent droplet forms a capillary bridge (hatched zone in FIG. 5). In the method of the invention, the continuous phase wets the channel, the spacer and the reagent droplet and the reactor droplet, so that plugs of the spacer and droplets of the reagent and/or reactor are surrounded by a thin film of the continuous phase and do not touch the channel. The capillary bridge is thus continuously linked to the other capillary bridge. The presence of the continuous phase close to the channel wall may be inferred from the boundaries of the other two components, which both tangentially curve away from the channel wall at the spacer plug/reactor droplet interfaces.

The presence of at least three phases means that an interfacial force γ between respectively the continuous phase/the spacer, the continuous phase/the reactor fluid, the spacer/the reactor fluid can be measured. Similarly, one can measure an interfacial force between respectively the continuous phase/the reagent fluid, the spacer/the reagent fluid.

The spacer droplet and the reactor droplets are preferably fully wet by the continuous phase. The condition on the spreading parameters $S\_i=\gamma\_jk-(\gamma\_ij+\gamma\_ik)$ where $(i,j,k)=(1, 2,3)$ are given in FIG. 1 from Torza and Mason, 1970 (Three-Phase Interactions In Shear and Electrical Fields, S.

TORZA AND S. G. MASON, Journal of Colloid and Interface Science, vol. 33, No. 1, May 1970).

On the chemical point of view, the continuous phase is substantially immiscible with the fluid of the reactor droplet and with the fluid of the reagent droplet the spacer fluid is substantially immiscible with the continuous phase, the reactor droplet fluid and the reagent droplet fluid One important characteristic of the method is that in step b) the reagent fluid is non-wetting. This means that the reagent fluid does not wet the channels walls and the injection walls.

Steps b) and c) of the method of the invention preferably comprise the following subsequent main stages:

i) Generation of a hanging reagent droplet, i.e. still connected to the reagent reservoir, having a controlled volume (step b)

ii) Detachment of the reagent droplet from injection point (step b)

iii) Contact of reagent droplet with reactor droplet and through the drainage of the continuous phase (step c)

iv) Droplet fusion either active or passive (step c)

The volume of the hanging reagent droplet is determined by the injection pressure, that is greater than the pressure implemented for moving the train.

Figure 6:
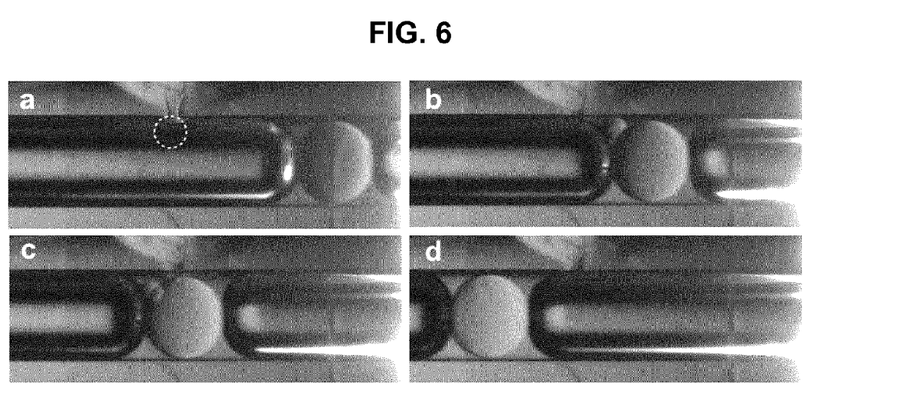
FIG. 6: Pictures of the main stages of a preferred self-synchronised fusion scheme of the invention: 6a: Reagent droplet generation; 6b: Reagent droplet detachment from nozzle; 6c: Droplet contact and continuous phase drainage; 6d: Droplet fusion

Pictures of the main stages of a preferred self-synchronized fusion scheme are reported in FIG. 6.

The method will be, in this paragraph, described by reference to the FIG. 6. In this particular embodiment, the reagent is added by a lateral inlet. The self-synchronization feature of this invention is shown in FIG. 6a, where a reagent droplet remains attached to the reagent reservoir, and thus forms a hanging droplet at the lateral inlet until the extremity of the spacer plug reaches the hanging reagent droplet. Then, detachment occurs and the recently formed reagent droplet goes into the continuous phase capillary bridge defined by the volume that separates the back tip of the spacer plug and the front tip of the reactor droplet (thus creating a mobile passive fusion chamber), as seen in FIG. 6b. The non-contamination feature of this method is shown in FIG. 6c, where the reagent droplet keeps its integrity after detachment. Then droplet fusion occurs away from the reagent droplet generation point (FIG. 6d), keeping uncontaminated the reagent solution reservoir. Additional evidence of the non-contamination feature is shown in FIG. 6e: when the reactor droplet passes under the lateral inlet, the reagent fluid meniscus experiences a retraction from the lateral inlet end, ensuring no contact between the reactor droplet and the reagent reservoir.

The zone in the continuous phase between the spacer plug and the reagent droplet forms a capillary bridge. In a preferred embodiment, the reagent droplet remains attached to the injection point and breaks-up when the capillary bridge in front of reactor droplet $A_{n+1}$ reaches the reagent droplet.

The method of the invention involves a new droplet formation mechanism: the interfacial tension induces break-up of the hanging droplet.

The reagent droplet detaches when the capillary force acting on the hanging droplet is larger than the capillary force that holds the hanging droplet. This mechanism defines a smallest reagent droplet size that can be produced.

The minimal volume of injected fluid is the necessary volume to obtain a hanging droplet that will break-up. Advantageously, the minimal radius of the reagent droplet, $r_{min}$ is defined by the following equation: $r_{min} \sim d \times \gamma_{12}/\gamma_{23}$ where d is the lateral inlet diameter (or the width or the height when the inlet is not round)

$\gamma_{12}$ is the surface tension between phase 1 (reagent) and phase 2 (continuous phase)

$\gamma_{23}$ is the surface tension between phase 2 (continuous phase) and phase 3 (spacer)

In a preferred embodiment, the volume of the droplet B is advantageously above 5 pL, more advantageously above 10 pL. In a preferred embodiment, the volume of droplet B is above 2 nL.

The maximal diameter will be determined by the man skilled in the art on a case by case basis. In particular, the maximal size of the reagent droplet is the size of the main channel to avoid any risk that the injected droplet cuts the spacer into two parts.

When the spacer fluid is a gas, in particular air, the maximal diameter formed by the interfacial tension induced droplet formation is mainly independent of flow rate of the continuous phase and corresponds about to the size of the tube where the train moves. The maximal volume of fluid that can be injected is the volume at which the droplet becomes a plug (that is diameter of the droplet is superior or equal to the channel diameter). Indeed, when the fluid does not form a droplet anymore but becomes a plug, there is a risk that the injected fluid split the spacer plug.

On the other hand, for a viscous spacer like mineral oil, the hanging droplet can be detached via a viscous force which is an increasing function of the fluid velocity, i.e. the continuous phase flow rate. The critical droplet size above which the shear-induced breakup occurs is inversely proportional to the velocity of the spacer and the viscosities of the continuous and spacer phases. Then the droplet is ejected from the spacer location and may finally contact to or fuse with the reactor droplet in a contamination free way. The delay time between droplet formation and expulsion can easily be determined by the skilled person, for instance by changing the location where active fusion is induced as well as the detection module location.

The volume of the droplet injected in step b) mainly depends on the channel size. In a particular embodiment, the volume is below 190 nL.

In a preferred embodiment, the ratio r/R, where r is the radius of the reagent droplet and R is the radius of the channel (or the half-width or half height when the channel is not round) ranges from 0.1 to 1, advantageously from 0.1 to 0.9, more advantageously from 0.2 to 0.7, even more advantageously from 0.25 to 0.60.

The lateral inlet diameter, d, (or the width or the height when the lateral inlet is not round) is small before the diameter, D, (or the width or the height when the channel is not round) of the channel. In particular, d<D. In preferred embodiments, d/D<0.5, in particular d/D ranges from 0.05 to 0.5.

Thus d depends on the channel size D. In a particular embodiment, d is below 200 µm, advantageously comprised between 50 µm and 200 µm for millifluidic conditions or comprised between 10 µm and 50 µm for microfluidic conditions.

Reagent droplet size, and thus reagent droplet volume, can be varied. Indeed, r_min/d≈1 (see FIG. 12), thus r_min/D≈d/D, and r_max/D≈0.5.

In the method of the invention, the presence of the spacer plug is necessary for this new break-up then coalescence mechanism.

The spacer plug shows a flat interface at the injection point. The length of the spacer L is preferably in accordance with the following equation:

$$L = D + \epsilon d$$

where

D and d are as defined above (or can be replaced by W, w the width or H, h the height when the channel or the lateral inlet is not round)

$\epsilon$ is a number greater than 2, in particular ranging from 2 to 100. This number, which depends on the ratio d/D, will be adjusted by the skilled person.

More preferably, the length of the spacer, L, is at least two times D, more preferably at least three times D.

Figure 7:
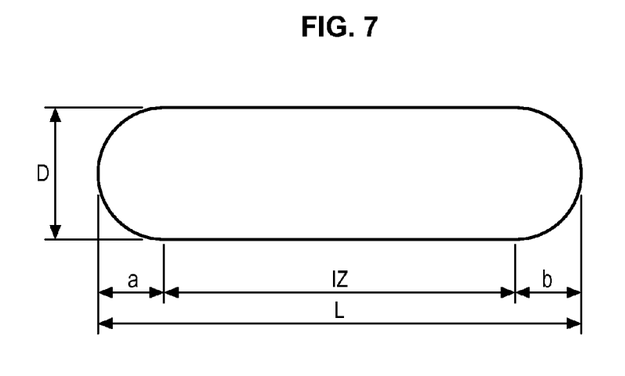
FIG. 7: Schematic representation of the spacer plug in the invention where the injection zone is IZ, D is the diameter of the channel, L the length of the spacer plug.

The injection preferably occurs when the injection point is in front of a flat surface of the spacer plug. The injection zone is schematically represented in FIG. 7: the injection zone IZ corresponds to the flat section of the spacer plug, where a≥D/2 and b≥D/2.

Advantageously, the spacer's tip is spherical.

After injection, the generated reagent droplets remain attached—during the passage of the spacer fluid—to the end of the injector (a lateral inlet in FIG. 6a) if the shear of the continuous thin film is insignificant to produce droplet neck rupture i.e. when the velocity of the spacer is low enough or the spacer viscosity is low like for a gas spacer. Visual inspection of captured videos indicates that droplet detachment occurs when the continuous capillary bridge—formed between the three phases—contacts the reagent hanging droplet (FIG. 6b). The interfacial tension between the spacer phase and the continuous phase provides the necessary force for inducing reagent droplet detachment. After detachment, the continuous capillary bridge acts as a mobile droplet fusion chamber (FIG. 6c), which allows contact between the reactor and the reagent droplets as well as drainage of the continuous phase between the two droplets which is necessary for droplet fusion (FIG. 6d). After fusion, the reagent phase and the reactor one then mix thanks to the internal flow induced by the motion of the reactor droplet (FIG. 6d).

During step b), when the reactor droplet detaches from the injection point, the reagent fluid meniscus experiences a retraction from the injector end, ensuring no contact between the reactor droplet and the reagent reservoir. The reagent fluid meniscus retracts from the injector end before the reactor droplet $A_{n+1}$ reaches the injection point and is still retracted when reactor droplet $A_{n+1}$ is at the injection point.

In order to increase the retraction of the meniscus, one preferably uses an injection device which comprises another compressible fluid and/or comprises a compressible material. For instance, the chamber of the injection device, hereafter called injection chamber, placed between the reagent reservoir and the injection point, may comprise the reagent fluid and air. When the reagent droplet breaks-up, detachment occurs and the meniscus experiences a retraction from the injector end due to the pressure change. This phenomenon can be emphasized by connecting the injection device to a capacitor or a capacitance: playing with resistance/capacitance, one can create pressure variations and thus emphasize meniscus retraction.

In a preferred embodiment, the reagent droplet is injected through a lateral inlet which emerges in the channel or tube where the droplet train is circulating. The injection device is preferably a picoinjector or a nanoinjector, but can also be any adapted mean. Preferably, the lateral inlet is a hole in the channel and the channel, on both lateral sides of the hole, is surrounded by a first coating which comprises an oil, said first coating is then coated by a polymer. The polymer can be a hydrophilic polymer, such a polyacrylic, or a hydrophobic polymer, depending on the nature of the reagent fluid.

The injection can be continuous or discontinuous, but is preferably discontinuous. A discontinuous injection will allow the control of the volume of the reagent droplet on case by case basis. Furthermore, with a discontinuous injection, one can choose the "target" reactor droplet and accordingly inject only when requested. Accordingly, before step b), the method advantageously comprises a step of detecting reactor droplet $A_{n+1}$. The reactor droplet $A_{n+1}$ can be detected by a detection means selected from the group consisting of optical means (such as laser beam, fluorescence, Raman spectroscopy, imaging), electrical means (such as impedance), magnetic means, radioactivity means, acoustic means. Furthermore, the method can comprise after the step of detecting reactor droplet $A_{n+1}$ but before step c) a step of singling out the detected droplet $A_{n+1}$ and adjusting accordingly the volume of the reagent droplet, which volume is null (no injection) or above 1 pL.

With a discontinuous injection, the method can be implemented even when the train of reactor droplets is irregular. An irregular train is defined by a variation of the size of the drops and/or the distance between the drops that compose the train. In the method of the invention, the train is a perfect train or an irregular train.

In a preferred embodiment, the injection of the reagent phase is actuated by a valve, in particular a solenoid valve, aligned to the lateral inlet by a polymeric manifold, the valve is connected to reagent reservoir. The device may further comprise a capacitor or a capacitance, in order to emphasize the meniscus retraction, and/or a resistance, in order to precisely control the injected volume.

The spacer can be a gas or a liquid immiscible with the reagent, reactor and continuous phases. In a first embodiment, the spacer is a gas selected from the group consisting of compressed air, argon, nitrogen, $CO_2$ or a combination of the aforementioned.

In this embodiment, the fluid of the droplet containing the reagent can be a fluid insoluble with the reagent droplet, such as mineral oil or silicone oil. In such a case, after injection, the system is a four-phase system. This four-phase train would be attractive for performing assays where difficulties exist in the solubility of a particular reagent in the reactor phase.

In a second embodiment, the spacer is an immiscible liquid with the continuous and the reactor and the reagent phase, such as mineral oil.

Usually, the channel of the micro/millifluidic devise is preferably made of fluorinated polymer, and more particularly of Teflon®. The continuous phase preferably comprises fluorinated oil and possibly a surfactant. The man skilled in the art is used with these components.

The man skilled in the art will select the fluid of the reactor droplet and of the droplet which contains the reagent on the case by case basis, depending on the reaction which is expected, on the basis of his technical knowledge. The reactor droplets are discrete, low-volume droplets, sometimes near-identical low-volume droplets, which travel through the channel at a common speed.

For example, one can use the following reagents-reactors:
Spore production: Potato Dextrose Agar plates
Growth media: Peptone-Glucose-Salts pH 4.6
Enzymatic activity: Bodipy FL EnzChek kit (in acetate buffer 4.6): This kit contains a starch substrate with quenched fluorescence. This substrate is efficiently degraded by amylase, digestion relieves the quenching and yields highly fluorescent fragments. The accompanying increase in fluorescence is proportional to amylase activity and can be monitored with fluorescence.

As examples of practical applications for the present method, one can recite combinatorial chemistry, chemical and biological screens, genetic sequencing. As example of biological screens, one can recite screening of microorganisms producing metabolites (enzymes, drugs). Thus the invention also refers to the method for its use in combinatorial chemistry, chemical and biological screens, genetic sequencing.

The three-phase train is generated inside a milli/microfluidic channel tube by using a T-junction by methods known by the skilled person, the liquid flow rates are controlled with pumps and the gas pressure with pressure controller.

In a preferred embodiment, the device is a millifluidic device.

The invention also relates to a millifluidic or microfluidic device comprising:
  A milli/microfluidic channel tube filled with a three-phase micro/millifluidic train comprising a continuous phase, at least two reactor droplets, and at least one spacer plug between two reactor droplets $A_n$ and $A_{n+1}$, wherein n is an integer 0
  An aperture opening on said channel, said aperture connected to a reservoir containing reagent in liquid phase
  A valve coupling said reservoir and said aperture
  A detector, placed upstream from said aperture.

The detector allows the synchronization of the opening of the valve with the coming of reactor droplet. In particular the valve is a solenoid valve. The volume of injected reactant is controlled by the open time (pulsation time) of the valve.

The equivalent circuit if the millifluidic or microfluidic device can be as follows: Two resistors R1 and R2 are in series. The junction between said two resistors is connected to an element IC in series with a resistor R3.

The element IC consists of a capacitor C1 and a resistor R4 disposed in parallel.

Figure 11:
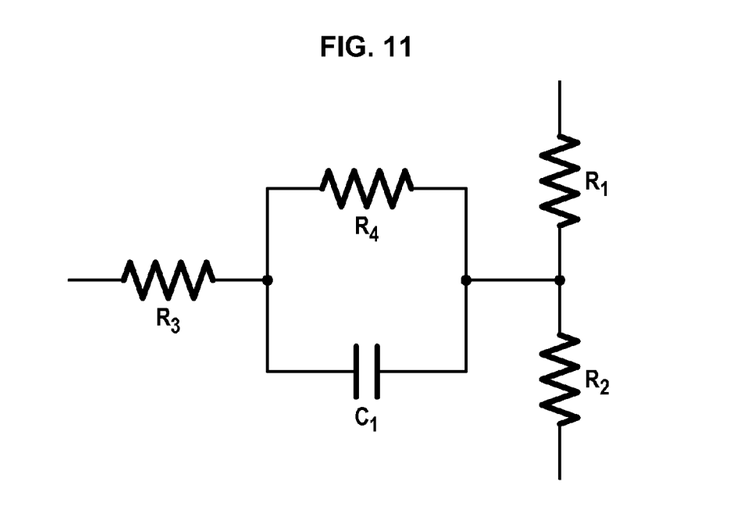
FIG. 11: Equivalent circuit of the device

The equivalent circuit is represented on FIG. 11.

In the following description the device will be described by reference to the device wherein the lateral inlet is a hole in the channel as illustrative but not limitative embodiment. Thus, the invention also relates to a millifluidic or microfluidic device comprising a channel tube pierced by a hole, an injection chamber formed by the space inside the coating surrounding the channel, on both lateral sides of the hole, a reagent reservoir and optionally a valve. Usually, the tube is made of Teflon®. The size of the hole is as described above for the lateral inlet.

Preferably, the device comprises a valve between the reagent reservoir and the injection chamber. In particular the valve is a solenoid valve. The volume of injected reactant is controlled by the open time (pulsation time) of the valve.

The device further comprises a resistance between the reagent reservoir and the injection chamber, more particularly between the reagent reservoir and the valve. In particular, the resistance can be a thin Teflon® tube connecting the reagent reservoir and the injection chamber, more particularly the valve. The resistance is used for providing a large flow resistance and thus for obtaining a constant added droplet volume. In millifluidic system, the tube has for example an internal diameter of 100 μm to 300 μm, more particularly 200 μm.

The channel, on both lateral sides of the hole, is surrounded by a polymeric coating. The coating is herein also called a manifold. The polymer can be any adapted polymer and is selected by the man skilled in the art, on the basis of his technical knowledge, depending on the nature of the reagent. In a particular embodiment, the polymer is an acrylic. Between the polymer and the channel, the coating advantageously further comprises an oily phase. The nature of the oil is preferably identical to the oil of the continuous phase.

The manifold is used to align the reagent reservoir and/or the valve and the hole. The reagent reservoir and/or valve is aligned and attached to the manifold by an appropriate means such as a mounting nut accessory.

The injection chamber is the space inside the manifold aligned with the pierced hole, in particular between the valve and the pierced hole. The equivalent circuit diagram of the injection chamber is a resistance and a capacitance in parallel.

In a preferred embodiment the capacitance is the compressible fluid present in the chamber of the injection device.

In another embodiment, the capacitance is a thin flexible membrane which will act as an artificial gas bubble. Such a membrane can be sealed to a hole drilled in the chamber.

In another embodiment, the capacitance is tube having a wall made of a material having a low elastic modulus.

The equivalent circuit of the device is represented on FIG. 11 wherein R1 and R2 correspond to the flow resistance of the droplet train on both sides of the injection point, R3 is the resistance described above and R4 is the resistance that arises from the flow of the reagent fluid through the injection chamber, while C1 is the capacitance inside the injection chamber.

The invention has for object a milli/microfluidic device whose equivalent circuit is represented on FIG. 11.

The device will now be described by reference to the device represented on FIG. 8, as illustrative but not limitative embodiment.

Figure 8:
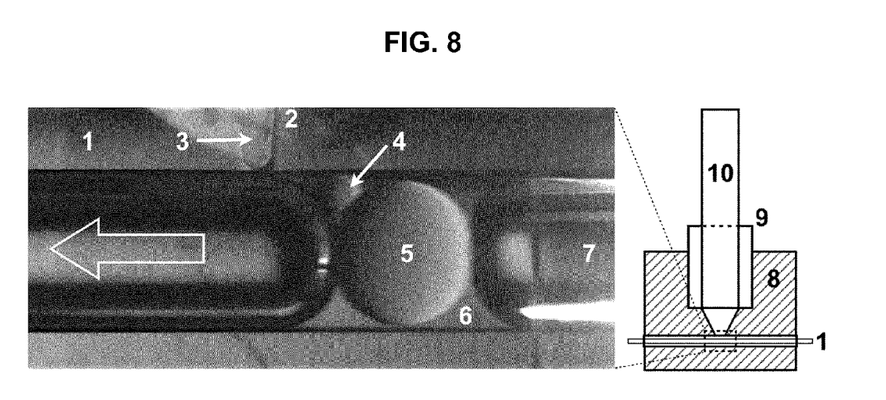
FIG. 8: Main elements of the self-synchronised fusion module. 1. Teflon tube. 2. Reagent reservoir. 3. Pierced hole. 4. Injected reagent droplet. 5. Reactor droplet. 6. Fluorinated oil continuous phase. 7. Compressed air spacer. 8. Acrylic manifold mount. 9. Mounting nut. 10. Solenoid valve.

Thus, the millifluidic or microfluidic device comprises a channel tube (FIG. 8, 1) pierced by a hole (FIG. 8, 3), an injection chamber formed by the space inside the acrylic manifold surrounding the channel (FIG. 8, 8), on both lateral sides of the hole, a reagent reservoir (FIG. 8, 2) and a valve (FIG. 8, 9).

The invention will be illustrated by the following non limitative examples.

Example 1: Three-Phase Millifluidic Train Generation

The three phase train consists of a continuous phase (fluorinated oil Novec HFE 7500+0.5% v/v perfluoro-octanol surfactant), a reactor droplet (Peptone-Glucose-Salts media, pH 4.6), and a spacer fluid (air or mineral oil). The train is generated inside a 750 um ID FEP Teflon® tube by using a T-junction, the liquid flow rates are controlled with syringe pumps and the gas pressure with a pressure controller. For the air spacer train, the flow rates of fluorinated oil and media are 6.5 and 7.5 ml/h, respectively and the air pressure is 1 Bar. For the mineral oil spacer train, the flow rates of fluorinated oil, media and mineral oil are 5, 5 and 10 ml/h, respectively.

The experimentally measured values of surface (pendant droplet method) are as follows:
  γ(HFE+PFO 0.5%)/Air: 12.5 mN/m+/−0.5 mN/m
  γ(HFE+PFO 0.5%)/Mineral Oil: 3.7 mN/m+/−0.5 mN/m
  γ(HFE+PFO 0.5%)/Water: 30.5 mN/m+/−0.5 mN/m For the experimental validation of the droplet ejection mechanism, fluorescein isothiocyanate FITC 1E-04 M are used as a reactor droplet fluid. Water droplets are injected into millifluidic trains with air or mineral oil spacers. Injection is triggered by reactor droplet fluorescence detection and actuated by a solenoid valve through pierced holes of three different radius (30, 50 and 90 um). Rmin is the minimum droplet radius that follows the proposed detachment mechanism and it is determined by image analysis of video captures of the injection process.

The values are reported in the table below:

TABLE 1

| Hole Radius (μm) | Air Rmin | Mineral Oil Rmin |
|---|---|---|
| 30 | 66 | 85 |
| 50 | 80 | 123 |
| 90 | 158 | 218 |

Error: ±4 μm on droplet radius, ±2 μm on hole radius

Graph for Detachment Model Prediction Vs. Measurements of Min Droplet Radius

Figure 12:
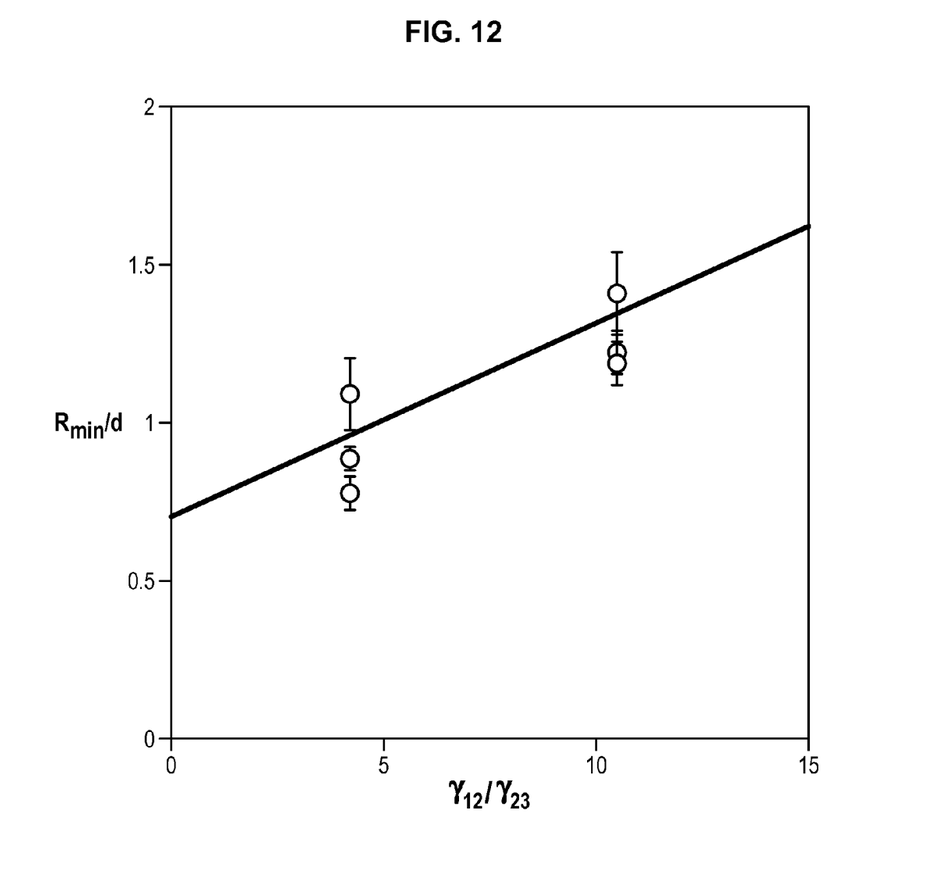
FIG. 12: Graph for detachment model prediction vs. measurements of min droplet radius

The results are reported in FIG. 12

Materials and Methods

1. Generation of a millifluidic droplet train on a 750 um ID FEP Teflon® tube. (Syringe pumps and/or pressure controller).
Train elements:
   a. Spacer fluid: Compressed air or mineral oil (length at least 3 times the tube internal diameter)
   b. Continuous phase: Fluorinated oil Novec HFE 7500+0.5% v/v perfluoro-octanol surfactant
   c. Reactor droplet: Peptone-Glucose-Salts media+BodipyFL (height between 80 and 85% the tube internal diameter)
2. Injection of reactant droplet (Methylene blue aqueous solution or acetate buffer (pH 4.5) solution+BodipyFL). The module elements are shown in FIG. 8.
Stages:
   a. Fluorescence signal detection of reactor droplet
   b. Injection of reactant droplet in front of reactor droplet (through a hole pierced in the tube). Injection actuated by a solenoid valve (VHS type, The Lee Co.) aligned to the pierced hole by an acrylic manifold (manifold mount kit, The Lee Co.). Assessment via image captures (GuppyPro firewire camera+Nikon 10× objective). FIG. 6*a*.
   c. Attachment of reactant droplet to pierced hole. FIG. 6*a*.
   d. Synchronisation: Reagent droplet detachment from pierced hole into continuous phase capillary bridge (mobile passive fusion chamber). Assessment via image captures. FIG. 6*b*.
   e. Contact between reagent droplet and reactor droplet on mobile passive fusion chamber. Assessment via image captures. FIG. 6*c*.
   f. Drainage of continuous phase on mobile passive fusion chamber. Assessment via image captures. FIG. 6*c*.
   g. Droplet fusion. Assessment via image captures and fluorescence signal monitoring. FIG. 6*d*.

Results

Reagent droplet injection test in millifluidic trains with air (FIG. 6) and mineral oil as spacer fluids, have shown the four typical stages of the self-synchronised scheme: reagent droplet generation, reagent droplet detachment from nozzle, droplet contact and continuous phase drainage and droplet fusion.

By using a methylene blue solution as a reagent solution, the mixing flow pattern after droplet fusion can be observed.

The fluorescence peak profile of a millifluidic train after addition of a BodipyFL 5x solution is obtained. The absence of gaps indicates dosage on all droplets, while the constant maximum level indicates a constant volume of the added droplets.

Implementation Example

Spores of *Aspergillus niger* mutant strains are diluted in PGS media after extraction to obtain an OD of 0.000375. This concentration allows the encapsulation of single spores inside PGS media reactor droplets. A millifluidic train with air spacers of 3105 reactor droplets is produced in a 30 m long FEP Teflon® tube (750 um ID). For train generation, the flow rates of Novec 7500 (with 0.5% v/v perfluoro-octanol surfactant) fluorinated oil and PGS media are 6.5 and 7.5 ml/h, respectively and the air pressure is 1 Bar. The train is circulated in back and forth directions by applying constant pressure (250 mBar). After the full train passes a laser droplet detector, the droplet train flow direction is automatically switched. In order to determine the enzymatic activity after 30 h of fungal growth at 30° C., 5 nL Bodipy FL droplets are injected into each droplet of the millifluidic train by using the module of the invention, applying a pressure of 250 mBar for train circulation, 300 mBar for reagent droplet addition, and generating 3 ms pulses of solenoid valve opening, for a 50 μm radius pierced hole. A 45 s delay between droplet addition and fluorescence detection is obtained by locating separating the addition and fluorescence modules by 30 cm. This delay ensures the collection of a single data point for each droplet within the linear section of the enzymatic activity curve, as shown by numerous preliminary tests. The fluorescence signal of the added train is shown in FIG. 9*b* (zoom). In this curve, the baseline corresponds to the signal of the empty droplets, while the peaks correspond to the fluorescence by amylase activity of the 558 droplets occupied with fungi.

Figure 9A:
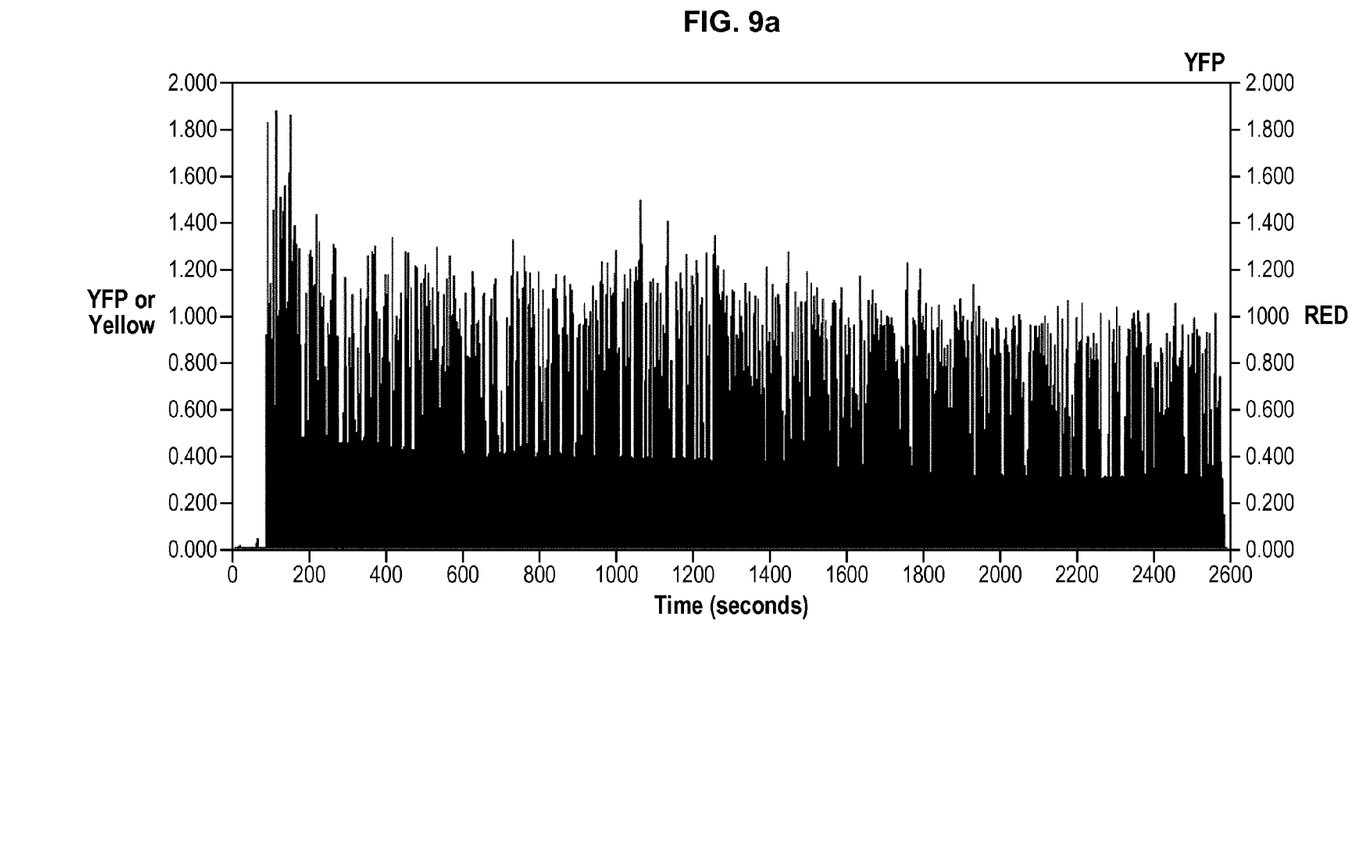
FIG. 9a: Fluorescence signal of the added fungal millifluidic train
Figure 9B:
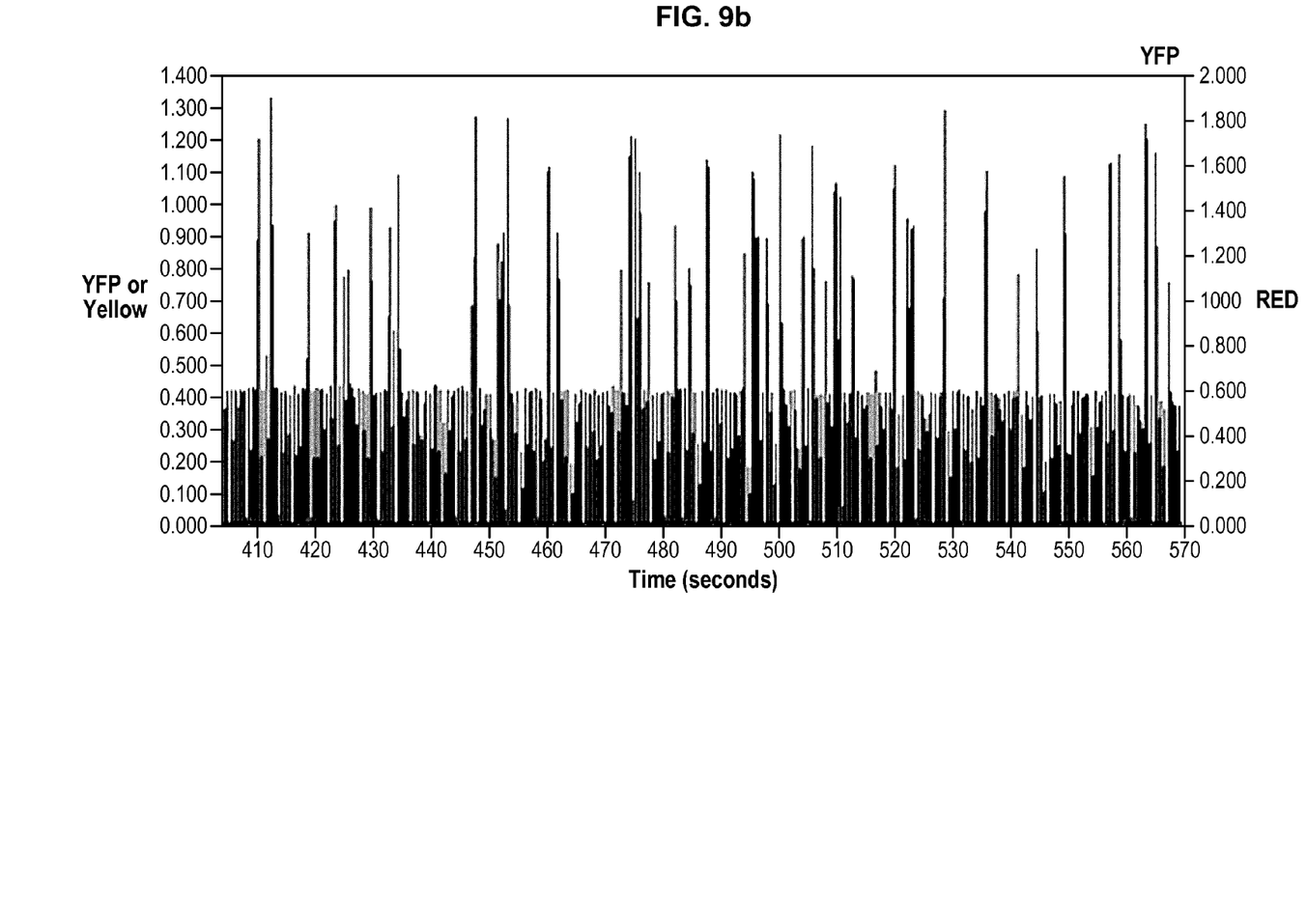
FIG. 9b: Fluorescence signal of the added fungal millifluidic train (zoom)

FIGS. 9*a* and 9*b* indicate the high quality of the addition module, expressed as the constant fluorescence intensity of the empty droplets.

Figure 10:
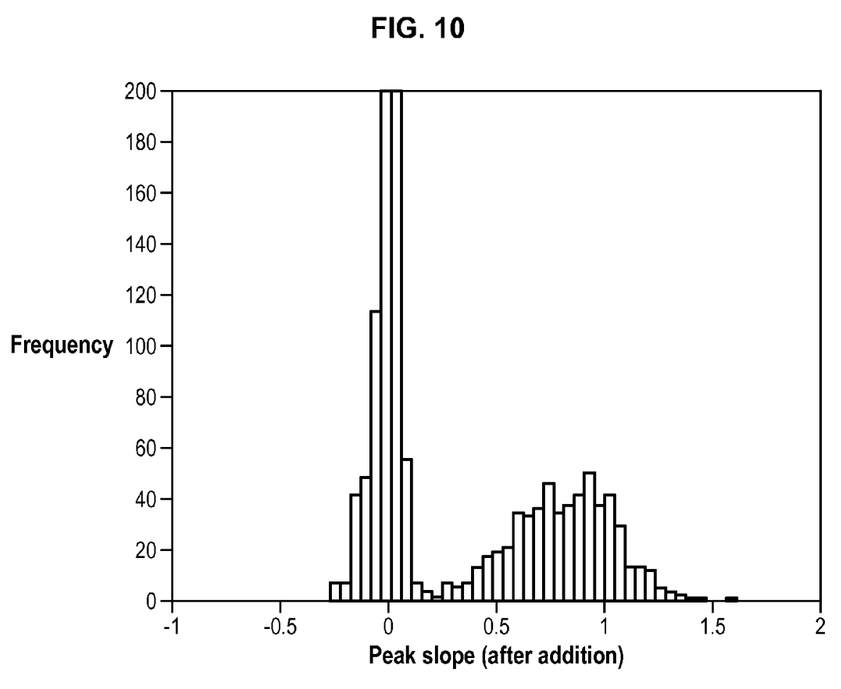
FIG. 10: Enzymatic activity of a *A. niger* mutant library

The enzymatic activity of the *Aspergillus niger* mutant library analysed with the millifluidic system is shown in FIG. 10, where a perfect differentiation between empty and occupied droplets was obtained, as well a wide distribution on the enzymatic activity of the library.

Example 2: Example of Variable Volume Injection

Figure 13:
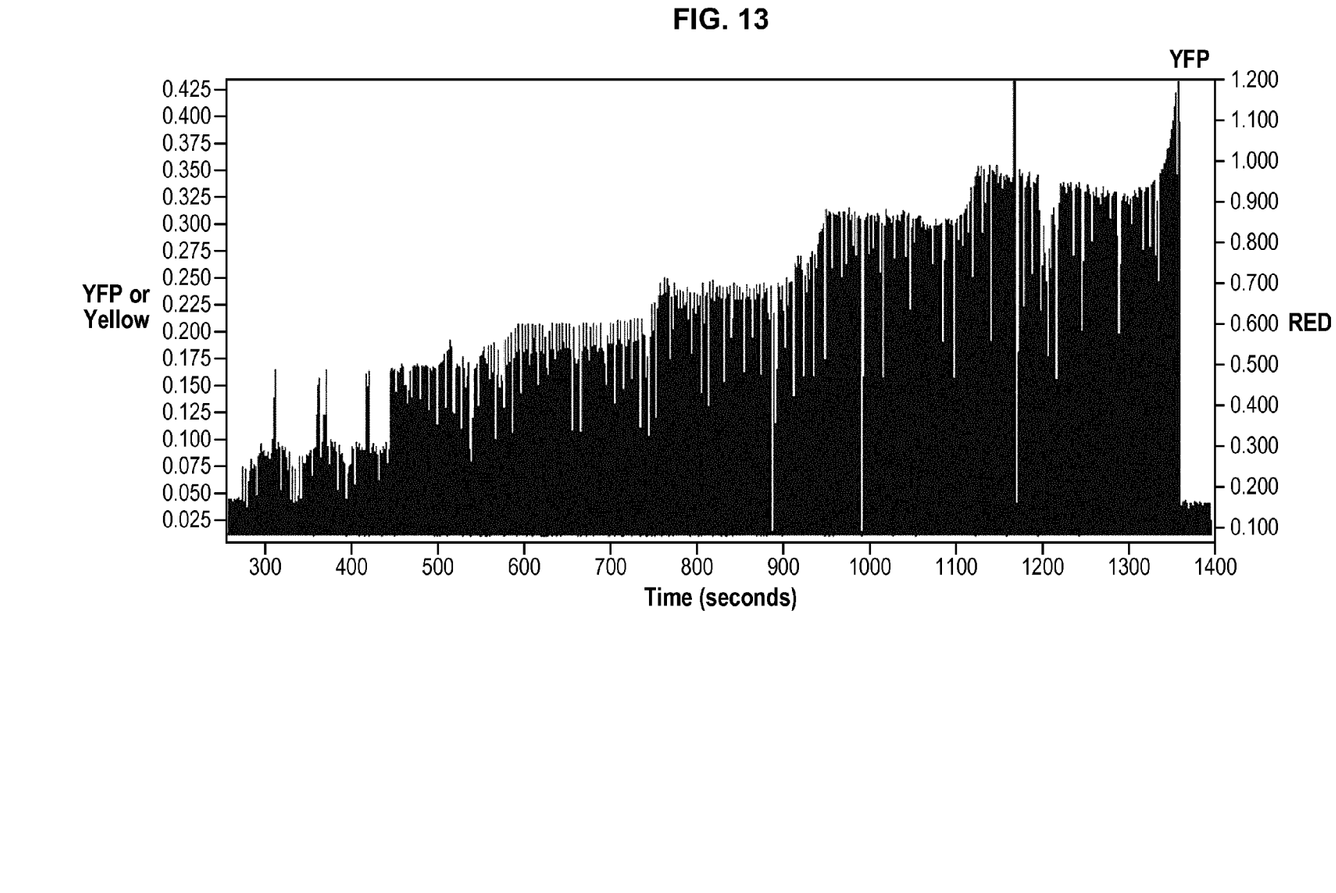
FIG. 13: Variable volume injection—fluorescence signal
Figure 14:
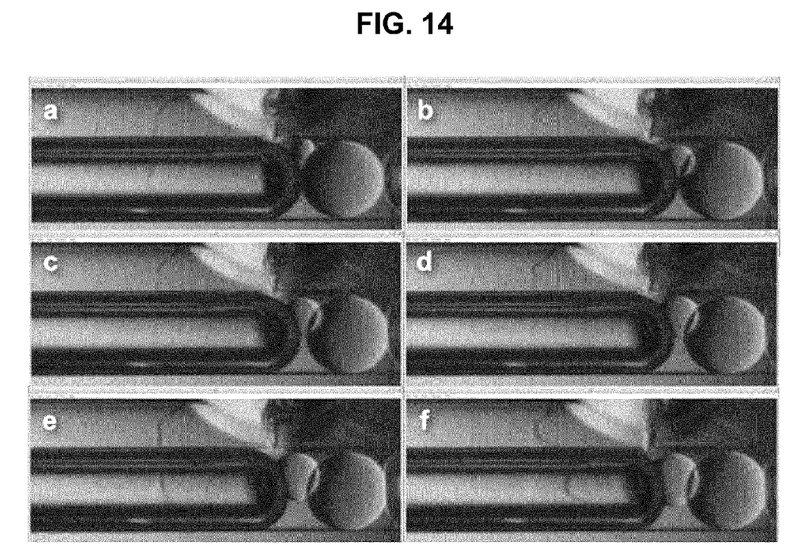
FIG. 14: Variable volume injection—increase on injected droplet size
Figure 15:
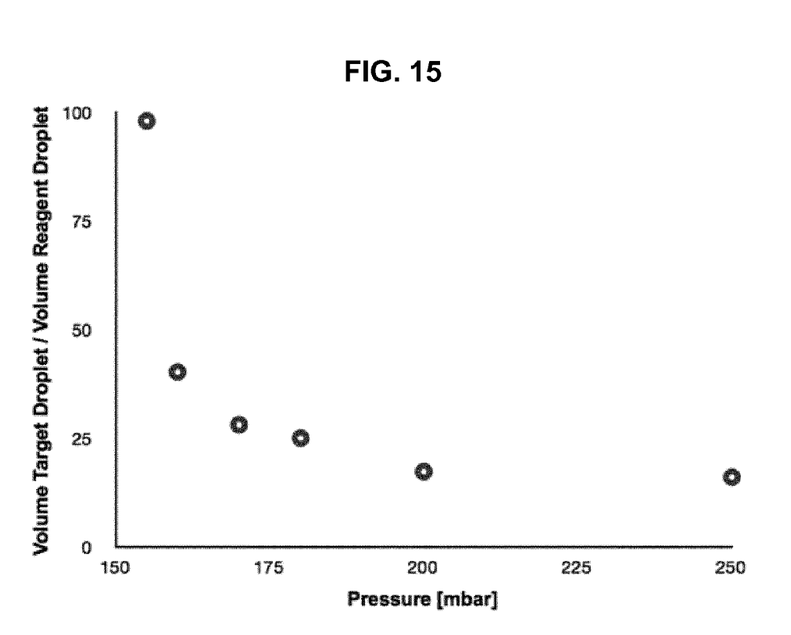

To determine the added droplet volume by fluorescence, fluorescein concentrated droplets are added into a millifluidic train formed by diluted fluorescein droplets with air bubbles as spacers. Millifluidic train generation conditions are identical to the presented in the previous example 1. Solenoid valve actuation is based on droplet detection by fluorescence. FITC fluorescein 1E-04 M droplets are injected into each droplet of the millifluidic train (FITC fluorescein 1E-06 M droplets) by using the module of this invention (pierced hole radius: 50 μm), applying 10 ms pulses of solenoid valve (VHS type, The Lee Co.) opening, a 150 mBar pressure for train circulation, and variable pressures from 150 to 300 mbar for reagent droplet addition. After complete millifluidic train injection, flow is reversed to record the fluorescence signal of the added droplets. The fluorescence signal of the injected train is shown in FIG. 13, where each step corresponds to a different pressure of reagent droplet addition. The increase of reagent droplet volume with increasing pressure is shown in FIG. 14, which correspond to snapshots of captured videos. A mass balance allows the quantification of the target droplet volume to reagent droplet volume ratio $(V_T/V_R)$ with the expression $V_T/V_R=(C_F-C_T)/(C_R-C_E)$, where $C_E$, $C_T$ and $C_R$ are the concentrations of the added, target and reagent droplets. Given the proportionality between fluorescein concentration and fluorescence peak height, $C_E$ and $C_T$ correspond to the fluorescence peak heights for the added and target droplets. With $C_R/C_T=100$, the calculated values for $(V_T/V_R)$-using the average peak height value for each step—are plotted in FIG. 15, as a function of the applied pressure reagent droplet addition. $V_T/V_R$ ratios from 98 to 16 were obtained in the pressure range studied, highlighting the flexibility of the developed module for producing reagent droplets over a wide range of volumes. This feature has potential applications for the generation of concentration gradients within micro- and millifluidic systems.

Example 3: Meniscus Retraction Increase

Figures 16A, 16B:
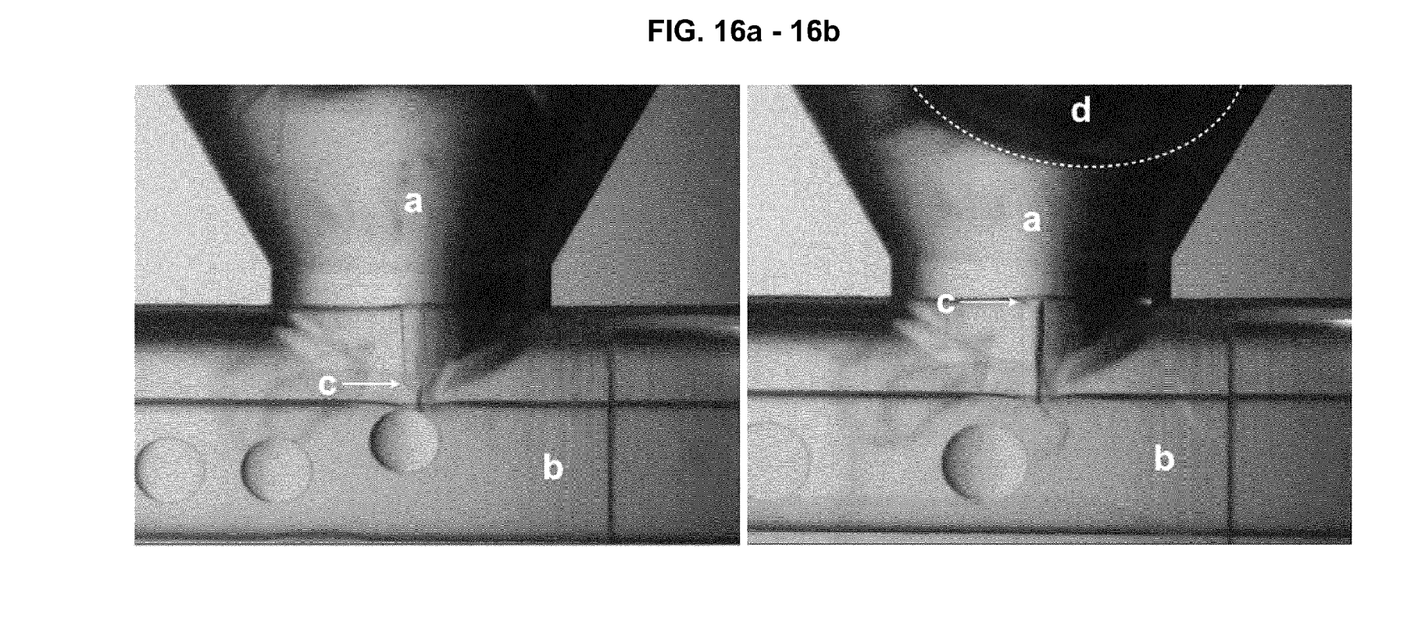

In order to demonstrate the meniscus retraction increase by the introduction of a capacitor in the injection system, an air bubble is introduced inside the reagent reservoir. The meniscus position after detachment during reagent droplet formation is recorded by video capture. FIG. 16 shows the maximum meniscus retraction under continuous reagent flow (water, 100 mBar applied pressure), through a 50 µm radius hole, on a Fluorinated oil Novec 7500+0.5% v/v perfluoro-octanol surfactant stream flowing at 2.5 ml/h. Compared with a parallel test performed without the air bubble (FIG. 16, left) where identical operational conditions are kept, meniscus retraction is larger when the air bubble is present (FIG. 16, right). This effect is due to the increase on the pressure change by the compressibility of the air bubble, after reagent droplet break-up.

The invention claimed is:

1. A method for fusing or contacting reactor and reagent droplets in a microfluidic or millifluidic device, comprising the steps of:
  (a) in a channel of said microfluidic or millifluidic system, generating a three-phase micro/millifluidic train comprising a continuous phase, at least one reagent droplet, at least two reactor droplets, and at least one spacer plug between two reactor droplets $A_n$ and $A_{n+i}$, wherein n is an integer>0, and wherein the continuous phase wets the channel, the spacer, the reagent droplet, and the spacer, and the reagent and reactor droplets do not touch the channel;
  (b) injecting with the help of a lateral inlet named injector, into the train, reagent in a non-wetting single droplet B, wherein said non-wetting droplet does not wet walls of the channel or the injector, and wherein said droplet B is generated in situ during the passage at the injection point of the spacer plug directly preceding reactor droplet, wherein the droplet B is detached from the injection point before the reactor droplet reaches the injection point with the formation of a reagent fluid meniscus at the injector end, and wherein the reagent fluid meniscus is retracted within the lateral inlet when the reactor droplet $A_{n+1}$ is at the injection point;
  (c) then, fusion or contact of the droplet B with reactor droplet away from the injection point;
  (d) when n>1, reiteration of steps (b) and (c).

2. The method of claim 1, wherein the reagent droplet remains attached to the injection point and breaks-up when the capillary bridge in front of reactor droplet $A_{n+1}$ reaches the reagent droplet.

3. The method of claim 1, wherein the ratio r/R, where r is the radius of the reagent droplet and R is the radius of the channel, ranges from 0.1 to 1.

4. The method of claim 1, wherein the volume of the droplet injected in step b) is above 1 pL.

5. The method of claim 1, wherein the ratio d/D where d is the diameter of the lateral inlet and D is the diameter of the channel for a cylindrical geometry, or the D is the height or the width of the channel for a planar geometry, ranges from 0.05 to 0.5.

6. The method of claim 1, wherein the injection is discontinuous.

7. The method of claim 6, wherein the reagent droplet is actuated by a valve, in particular a solenoid valve.

8. The method of claim 1, wherein before step b), reactor droplet $A_{n+1}$ is detected by a detection means selected from the group consisting of optical means, electrical means, magnetic means, radioactivity means, acoustic means.

9. The method of claim 1, wherein step b) further comprises after the step of detecting reactor droplet $A_{n+1}$ but before step c) a step of singling out the detected droplet $A_{n+1}$ and adjusting accordingly the volume of the reagent droplet, which volume is null or above 1 pL.

10. The method of claim 1, wherein the spacer is a gas or a liquid immiscible with the continuous and the reactor and the reagent phase.

11. The method of claim 10, wherein the spacer is an immiscible liquid, such as mineral oil.

12. The method of claim 1, wherein the device is a millifuidic device.

13. The method of claim 1 for its use in combinatorial chemistry, chemical and biological screenings, genetic sequencing.

14. A milli/microfluidic device comprising:
  A milli/microfluidic channel tube filled with a three-phase micro/millifluidic train comprising a continuous phase, at least two reactor droplets, and at least one spacer plug between two reactor droplets $A_n$ and $A_{n+i}$, wherein n is an integer>0
  An aperture opening on said channel, said aperture is connected to a reservoir containing reagent in liquid phase
  A valve coupling said reservoir and said aperture and
  A detector, placed upstream from said aperture and configured to detect the reactor droplet $A_{n+1}$ before injecting a reagent droplet.

15. A milli/microfluidic device according to claim 14, comprising an equivalent circuit including the following:
  two resistors R1 and R2 in series, wherein the junction between said two resistors is connected to an element IC in series with a resistor R3; and
  the element IC consists of a capacitor C1 and a resistor R4 disposed in parallel.

* * * * *